United States Patent [19]
Brose

[11] Patent Number: 4,643,714
[45] Date of Patent: Feb. 17, 1987

[54] SINGLE NEEDLE APPARATUS

[75] Inventor: Tom L. Brose, Lakewood, Colo.

[73] Assignee: Cobe Laboratories, Inc., Lakewood, Colo.

[21] Appl. No.: 762,562

[22] Filed: Aug. 5, 1985

[51] Int. Cl.$^4$ ............................................. A61M 1/03
[52] U.S. Cl. ...................................... 604/4; 604/118; 128/DIG. 13
[58] Field of Search ........................................ 604/4–6, 604/118; 128/DIG. 13

[56] References Cited
U.S. PATENT DOCUMENTS

| | | | |
|---|---|---|---|
| Re. 29,346 | 8/1977 | Kopp | 128/214 |
| 3,830,234 | 8/1974 | Kopp | 128/214 |
| 4,063,554 | 12/1977 | Willock et al. | 128/214 |
| 4,231,366 | 11/1980 | Schael | 128/214 |
| 4,464,164 | 8/1984 | Troutner et al. | 604/5 |
| 4,490,134 | 12/1984 | Troutner | 604/4 X |
| 4,514,295 | 4/1985 | Mathieu et al. | 604/5 |
| 4,552,552 | 11/1985 | Polaschegg et al. | 604/4 |

*Primary Examiner*—Dalton L. Truluck

[57] ABSTRACT

Automatically monitoring the volume of blood removed from a patient during the arterial phase of a control cycle of single venipuncture needle apparatus, and switching from the arterial phase to the venous phase when a predetermined stroke volume has been achieved.

14 Claims, 3 Drawing Figures

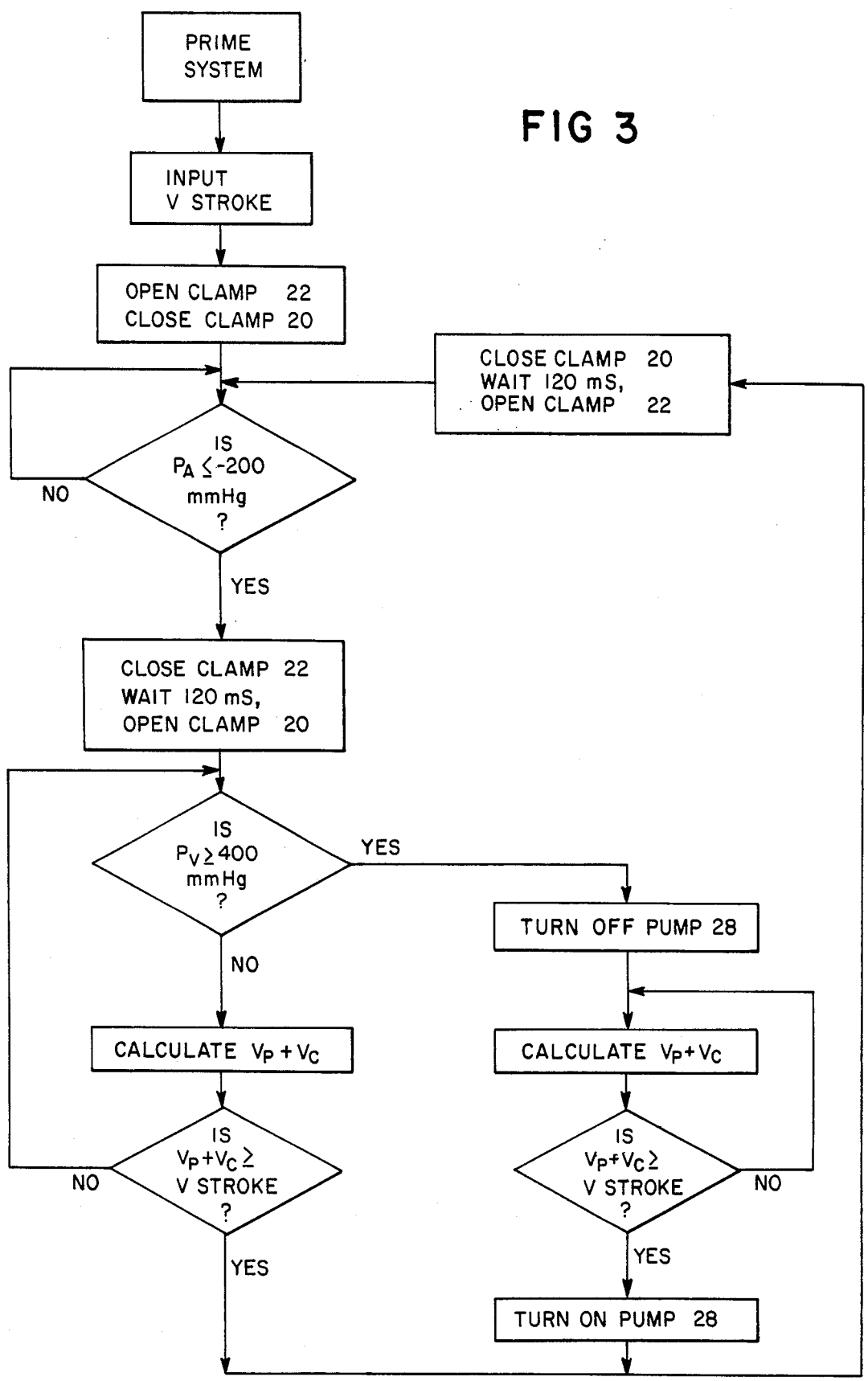

SINGLE NEEDLE APPARATUS

FIELD OF THE INVENTION

The invention relates to single venipuncture needle apparatus.

BACKGROUND OF THE INVENTION

Single venipuncture needles have been used to cyclically remove untreated blood from a patient and return treated blood to a patient, e.g., in conjunction with fluid flow transfer devices such as dialyzers. The control cycles consist of the arterial phase and the venous phase. In the arterial phase the blood is pumped from the patient through the needle and an arterial line while a venous line is clamped shut. In the venous phase the blood is returned to the patient through the venous line and the needle while the arterial line is clamped shut.

One or two pumps can be used, and the pumps can be used continuously or intermittently. The pumps and clamps used to control the flow in past systems have been switched between the arterial and venous phases of the cycle by responding to maximum and minimum pressures (e.g., Schael U.S. Pat. No. 4,231,366; Kopp U.S. Pat. No. Re. 29,346), by switching after given periods of time (e.g., Willock et al. U.S. Pat. No. 4,063,554) or by using both pressure and time (e.g., Kopp U.S. Pat. No. Re. 29,346; Kopp U.S. Pat. No. 3,830,234).

The arterial and venous lines are typically made of flexible tubing that expands and contracts slightly with changes in pressure. There might be as much as four feet of flexible tubing between the clamps and the venipuncture needle, and immediately following switching of the clamps from the venous phase to the arterial phase, the extra volume of blood in the expanded venous tube can be pushed into the arterial tube, causing recirculation. Similarly, a small amount of treated blood can be transferred from the venous line to the arterial line during switching from the arterial phase to the venous phase. Stroke volume is the amount of blood removed from a patient during a single cycle. Some operators of single needle apparatus have been interested in knowing the stroke volume being achieved during operation to make sure that it is large enough, and they have in instances estimated it by measuring the length of the cycle with a stop watch and multiplying the time times the pumping rate of the blood pump.

SUMMARY OF THE INVENTION

In one aspect the invention features automatically monitoring the volume of blood removed from a patient during the arterial phase of a control cycle of single venipuncture needle apparatus, and switching from the arterial phase to the venous phase when a predetermined stroke volume has been achieved. This has been found to be an effective mechanism for triggering switching from the arterial phase to the venous phase in terms of overall performance, and has the advantage of guaranteeing that desired stroke volumes are achieved.

In preferred embodiments the apparatus is switched from the venous phase to the arterial phase when the pressure between the arterial clamp and the blood pump reaches a minimum pressure set point; an arterial chamber is located between the arterial clamp and the pump, and the monitoring of the blood removed from the patient includes both the amount pumped by the pump and the amount pulled into the chamber owing to pressure recovery in the chamber during the arterial phase; and there is a venous chamber between the fluid flow transfer device and the needle, and the pressure therein is monitored so that if a maximum pressure limit is reached, the pump is stopped, in order to prevent damage.

In another aspect the invention features providing delay periods in which both the venous and arterial clamps are closed during switching between the venous and arterial phases, to reduce recirculation of treated blood.

Other advantages and features of the invention will be apparent from the following description of the preferred embodiment and from the claims.

DESCRIPTION OF THE PREFERRED EMBODIMENT

The drawings will be briefly described first.

Drawings

Figure 1:
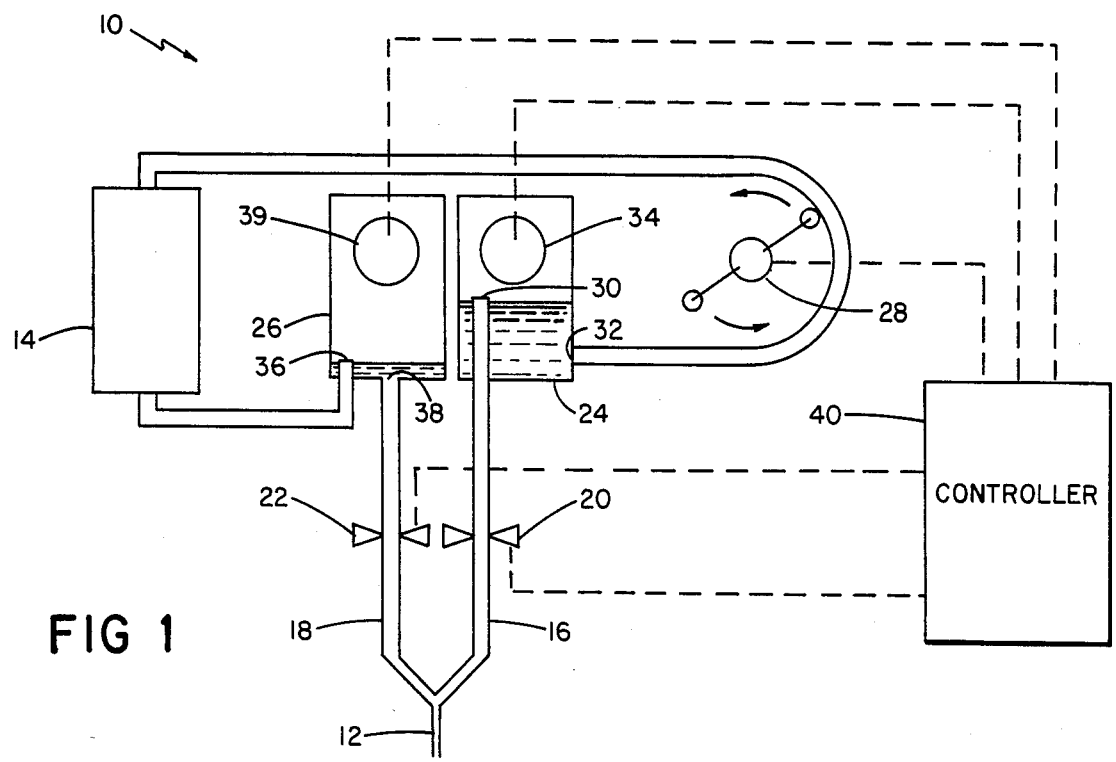

FIG. 1 is a diagrammatic representation of single venipuncture needle apparatus according to the invention.

Figure 2:
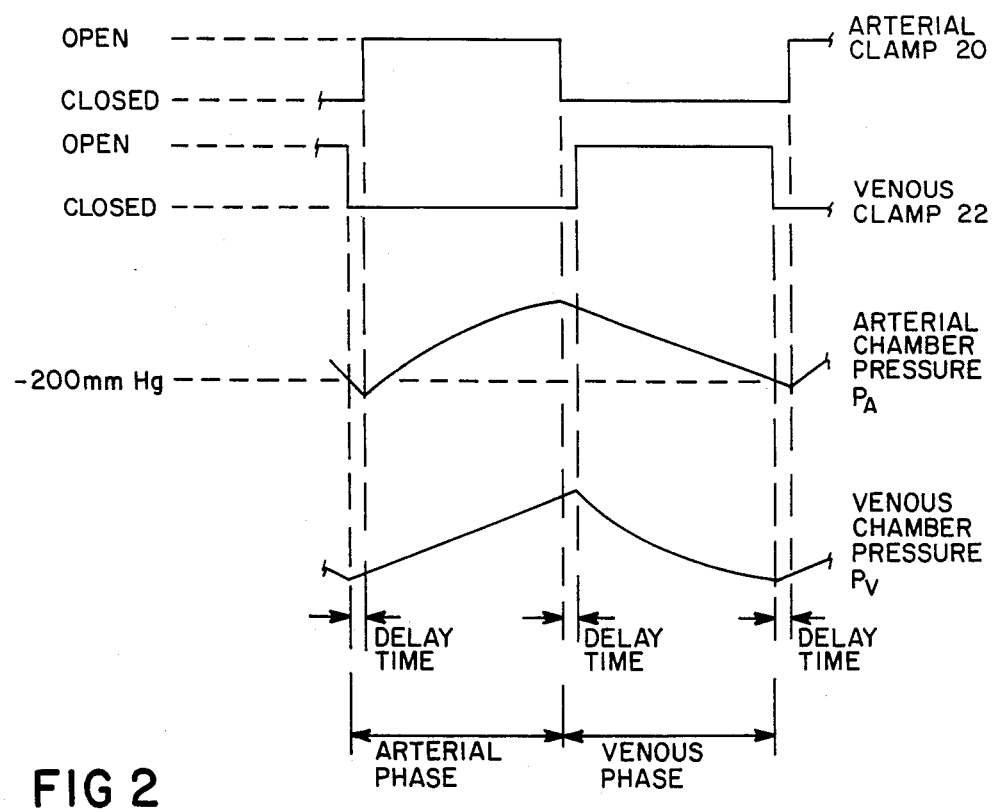

FIG. 2 includes graphs presenting clamp switching positions and arterial and venous chamber pressures during the arterial and venous phases of the FIG. 1 apparatus.

FIG. 3 is a flow chart describing the automatic control program of the FIG. 1 apparatus.

Structure

Referring to FIG. 1, there is shown single venipuncture needle apparatus 10 for removing untreated blood from a patient (not shown) through needle 12, treating it in fluid flow transfer device 14 (a hollow fiber dialyzer) and returning it to the patient through needle 12. Arterial line 16 is connected to needle 12 for removal of blood from it. Venous line 18 is also connected to needle 12 for return of blood to it. Arterial clamp 20 and venous clamp 22 are located on lines 16, 18, respectively, for alternately blocking flow through the lines. Arterial line 16 is connected to arterial chamber 24, and venous line 18 is connected to venous chamber 26. Peristaltic pump 28 is connected between arterial chamber 24 and fluid flow device 14. Inlet passage 30 of arterial chamber 24 ends at a predetermined distance above the floor of chamber 24 to control the initial level of liquid in it and the initial volumes of air and liquid in it. Arterial chamber outlet 32 is near the bottom of chamber 24. In the upper portion of arterial chamber 24 is arterial pressure sensor 34. Venous chamber 26 similarly has inlet 36 at a predetermined distance above the floor of chamber 26, outlet 38 at the bottom, and venous pressure sensor 39 in the upper portion.

Arterial clamp 20, venous clamp 22 and pump 28 are electrically connected to receive control signals from microprocessor-based electronic controller 40. Arterial pressure sensor 34 and venous pressure sensor 39 are electrically connected to controller 40 to provide it with signals indicating the arterial and venous chamber pressures.

Operation

Prior to use with a patient, single needle apparatus 10 is primed with saline solution by attaching a saline bag to venous line 18 and operating pump 28 in the reverse (clockwise) direction. This causes the saline solution to be pulled into venous chamber 26. The amount of fluid in chamber 26 is automatically determined by the height of inlet 36. Once the saline solution reaches the opening of inlet 36, the fluid and air volumes in chamber 26 do not change, and saline solution then travels through fluid flow transfer device 14 and the tubing of blood pump 28 to arterial chamber 24. In the same manner as in venous chamber 26, the fluid level in arterial chamber 24 is automatically set by the height of inlet 30. The saline solution then travels through arterial line 16. Once all air has been removed from fluid flow transfer device 14, blood pump 28 is stopped, and arterial line 16 is connected to needle 12, already inserted into the patient. The arterial side of needle 12 is then unclamped, and blood pump 28 is started in the forward direction, drawing blood from the patient into apparatus 10 and replacing the saline solution in it by forcing the saline solution out of the end of venous line 18. Once apparatus 10 has filled with blood, the blood pump is stopped; the end of venous line 18 is connected to needle 12, and the venous side of the needle is unclamped.

After the priming operation has been completed, pump 28 is continuously operated during both phases. The first phase is a venous phase in which arterial clamp 20 is closed, venous clamp 22 is open, and pump 28 draws the fluid level down in arterial chamber 24 as it passes through fluid flow transfer device 14 (FIG. 3). As the fluid level in arterial chamber 24 decreases, the pressure in chamber 24 also decreases and once pressure sensor 34 senses that the pressure has reached the minimum set point of −200 mm Hg, controller 40 closes venous clamp 22 to begin the arterial phase. Arterial clamp 20 is maintained closed until 120 ms after venous clamp 22 has closed, to permit the extra capacity of expanded venous line 18 between clamp 22 and needle 12 to be discharged into the patient instead of being recycled into arterial line 16. After arterial clamp 20 has been opened, blood is drawn into chamber 24, increasing the level therein. During this time, controller, 40 calculates the volume of blood being removed from the patient during the arterial phase by periodically adding the volume drawn since the beginning of the arterial phase by pump 28 ($V_p$) to the volume pulled into arterial chamber 24 owing to the pressure recovery therein ($V_c$). The volume of liquid pulled into chamber 24 owing to pressure recovery is equal to the reciprocal of the difference in pressure currently sensed by pressure sensor 34 and the lowest pressure sensed at the beginning of the arterial phase times the compliance constant for chamber 24 based upon Boyle's law (pressure X volume of air = a constant), where the pressure is corrected for the altitude at which the machine is used. As is indicated in FIG. 3, controller 40 periodically calculates $V_p + V_c$ and then compares the sum with the desired stroke volume ($V_{stroke}$) entered into controller 40 at the beginning of the operation. Once the sum of $V_p$ and $V_c$ is greater than or equal to the stroke volume, apparatus 10 switches from the arterial phase to the venous phase by closing arterial clamp 20. During the arterial phase, controller 40 determines the average time to achieve stroke volume in the immediately prior strokes, and if the stroke volume has not been reached after being in the arterial phase for the average time plus a predetermined period (e.g., 5 or 10 seconds), an alarm is sounded. (This step is not shown on FIG. 3.) Once again there is a 120 ms delay period before venous clamp 22 is opened to reduce recirculation effects. The venous phase continues until the pressure in arterial drip chamber 24 reaches −200 mm Hg once again, and so on.

During the arterial phase, if the pressure in venous chamber 26 reaches +400 mm Hg, controller 40 automatically turns off blood pump 28 to prevent damage to fluid flow transfer device 14. Blood still continues to be pulled into arterial chamber 24, owing to the pressure recovery therein, and when the desired stroke volume has been removed from the patient, pump 28 is turned on again, and the process continues.

−200 mm Hg is chosen as set point for switching between the venous and the arterial phases, so that the minimum arterial pressure is high enough to avoid hemolysis (thought to occur at lower pressures) and to avoid degassing in chamber 24.

OTHER EMBODIMENTS

Other embodiments of the invention are within the scope of the following claims.

What is claimed is:

1. Single needle blood treating apparatus comprising
a single venipuncture needle for alternately removing untreated blood from and returning treated blood to a patient,
an arterial line connected to said needle for removal of blood therefrom,
a venous line connected to said needle for return of blood thereto,
a fluid flow transfer device connected to said venous and arterial lines,
venous and arterial clamps on said venous and arterial lines for blocking flow through said lines,
a pump between said arterial and venous clamps for transporting blood through said arterial and venous lines,
an arterial pressure sensor connected to sense the pressure between said arterial clamp and said pump,
a chamber on said arterial line between said arterial clamp and said pump,
control means for alternately maintaining said arterial clamp open and said venous clamp closed during an arterial phase and maintaining said arterial clamp closed and said venous clamp open during a venous phase,
said control means including means responsive to said arterial pressure sensor for switching from said venous phase to said arterial phase when said pressure sensed by the arterial pressure sensor reaches a predetermined minimum value, and
means for automatically monitoring the volume of blood removed from said patient during said arterial phase and for causing said control means to switch to said venous phase after a predetermined volume of blood has been removed from said patient,
said means for monitoring including means for determining the amount of blood pumped by said pump since the beginning of the arterial phase and the amount of blood caused to flow into said chamber owing to pressure recovery in said chamber.

2. The apparatus of claim 1, further comprising a venous chamber between said fluid flow transfer device and said venous clamp.

3. The apparatus of claim 2, further comprising a venous pressure sensor in said venous chamber.

4. The apparatus of claim 2 wherein said arterial chamber has its inlet positioned at a predetermined position above its outlet so that during priming of said device during reverse flow, the liquid in said chamber rises to the level of said inlet, and a predetermined amount of air is provided in said arterial chamber.

5. The apparatus of claim 1, further comprising means for entering the value of said predetermined volume into said control means between minimum and maximum stroke volumes.

6. The apparatus of claim 3, further comprising means for comparing said pressure in said venous chamber with a predetermined upper limit and for stopping said pump upon sensing that the venous pressure is greater than or equal to said upper limit, and means for restarting said pump after said predetermined volume has been removed from said patient.

7. The apparatus of claim 1, further comprising means for delaying the opening of said venous clamp during the beginning of said venous phase and for delaying the opening of said arterial clamp during the beginning of said arterial phase to avoid recirculation of treated blood from said venous line to said arterial line.

8. The apparatus of claim 1 further comprising means to provide an alarm after a time period based upon the average time of prior arterial phases if said predetermined volume has not been reached yet.

9. A method of alternately removing and returning blood through a single venipunctive needle used in conjunction with an arterial line and a venous line connected to a fluid flow transfer device, said method comprising
providing arterial and venous clamps on said arterial and venous lines, a pump to transport blood through said arterial line, venous line and fluid flow transfer device, and a chamber on said arterial line between said arterial clamp and said pump,
alternately maintaining said arterial clamp open and said venous clamp closed during an arterial phase and maintaining said arterial clamp closed and said venous clamp open during a venous phase,
monitoring the volume of blood removed from said patient during said arterial phase, said monitoring including determining the amount of blood pumped by said pump since the beginning of the arterial phase and the amount of blood caused to flow into said chamber owing to pressure recovery in said chamber,
switching from said arterial phase to said venous phase after a predetermined volume of blood has been removed from said patient,
sensing the pressure between said arterial clamp and said pump, and
switching from said venous phase to said arterial phase when said pressure sensed reaches a predetermined minimum value.

10. The method of claim 9 wherein said arterial chamber has its inlet positioned at a predetermined position above its outlet, and further comprising priming said device by causing reverse flow, the liquid in chamber rising to the level of said inlet, a predetermined amount of air being provided in said arterial chamber.

11. The method of claim 9 further comprising providing automatic control means and entering the value of said predetermined volume into said control means between minimum and maximum stroke volumes.

12. The method of claim 9, further comprising comparing the pressure in said venous line with a predetermined upper limit, stopping said pump upon sensing that the venous pressure is greater than or equal to said upper limit, and restarting said pump after said predetermined volume has been removed from said patient.

13. The method of claim 9, further comprising delaying the opening of said venous clamp during the beginning of said venous phase and delaying the opening of said arterial clamp during the beginning of said arterial phase, to avoid recirculation of treated blood from said venous line to said arterial line.

14. The method of claim 9 further comprising providing an alarm after a time period based upon the average time of prior arterial phases if said predetermined volume has not been reached yet.

* * * * *